US011056241B2

(12) United States Patent
Utsunomiya et al.

(10) Patent No.: US 11,056,241 B2
(45) Date of Patent: Jul. 6, 2021

(54) RADIOTHERAPY PLANNING APPARATUS AND CLINICAL MODEL COMPARISON METHOD

(71) Applicant: Toshiba Medical Systems Corporation, Otawara (JP)

(72) Inventors: Kazuki Utsunomiya, Nasushiobara (JP); Kazuhisa Murakami, Tsu (JP); Longxun Piao, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 710 days.

(21) Appl. No.: 15/855,046

(22) Filed: Dec. 27, 2017

(65) Prior Publication Data
US 2018/0182495 A1 Jun. 28, 2018

(30) Foreign Application Priority Data

Dec. 28, 2016 (JP) ............................... JP2016-255330
Dec. 26, 2017 (JP) ............................... JP2017-248638

(51) Int. Cl.
*G16H 50/50* (2018.01)
*G16H 50/70* (2018.01)
*G16H 20/40* (2018.01)

(52) U.S. Cl.
CPC .......... *G16H 50/50* (2018.01); *G16H 20/40* (2018.01); *G16H 50/70* (2018.01)

(58) Field of Classification Search
None
See application file for complete search history.

(56) References Cited

U.S. PATENT DOCUMENTS

| 6,151,383 A | 11/2000 | Xue et al. |
| 2003/0101076 A1 | 5/2003 | Zaleski |
| 2012/0059779 A1* | 3/2012 | Syed .................. G06N 20/00 706/12 |

(Continued)

FOREIGN PATENT DOCUMENTS

| JP | 2000-195696 | 7/2000 |
| JP | 2005-505817 | 2/2005 |

(Continued)

OTHER PUBLICATIONS

Han et al., How to Develop, Validate, and Compare ClinicalPrediction Models Involving Radiological Parameters: Study Design and Statistical Methods, Jan. 14, 2016, Korean Journal of Radiology, 17.3, 339-350 (Year: 2016).*

(Continued)

*Primary Examiner* — Devin C Hein
(74) *Attorney, Agent, or Firm* — Oblon, McClelland, Maier & Neustadt, L.L.P.

(57) ABSTRACT

According to one embodiment, a radiotherapy planning apparatus includes processing circuitry and a display. The processing circuitry calculates, by applying patient information to each of a plurality of analysis models relating to clinical practice, analysis results based on the analysis models. The processing circuitry compares each of the analysis results with an actual clinical result relating to a comparison target patient, and generates evaluation information to evaluate a change between the analysis models. The display displays the evaluation information.

20 Claims, 13 Drawing Sheets

(56) References Cited

U.S. PATENT DOCUMENTS

| | | | |
|---|---|---|---|
| 2012/0284212 A1* | 11/2012 | Lin | G06N 20/00 |
| | | | 706/12 |
| 2014/0195472 A1 | 7/2014 | Kawagishi | |
| 2014/0222784 A1 | 8/2014 | Handler et al. | |
| 2014/0279754 A1 | 9/2014 | Barsoum et al. | |
| 2015/0227714 A1* | 8/2015 | Hayakawa | G16H 50/70 |
| | | | 705/3 |
| 2018/0039731 A1* | 2/2018 | Szeto | G16B 20/00 |

FOREIGN PATENT DOCUMENTS

| | | | |
|---|---|---|---|
| JP | 2014-147659 | 8/2014 | |
| JP | 2016-505973 | 2/2016 | |
| JP | 2016-519807 | 7/2016 | |
| WO | WO-2006113747 A2 * | 10/2006 | G01N 33/57415 |

OTHER PUBLICATIONS

Blankenburg et al., Troponin I and cardiovascular risk prediction in the general population: the BiomarCaRE consortium, May 12, 2016, European Hear Journal, doi:10.1093/eurheartj/ehw172 (Year: 2016).*

* cited by examiner

| Model ID | Algorithm | Model name | Current version | Old version |
|---|---|---|---|---|
| 001 | Decision tree | Weight loss | 1.0 | – |
| 002 | Decision tree | Weight loss | 2.0 | 1.0 |
| 003 | Decision tree | Weight loss | 3.0 | 2.0 |
| 004 | Regression tree | Tumor response | 1.0 | – |
| 005 | Regression tree | Tumor response | 1.1 | 1.0 |

F I G. 2

| Parameter ID | Model ID | Parameter name | Operator | Condition value | False branch | True branch | Certainty factor of false branch | Certainty factor of true branch |
|---|---|---|---|---|---|---|---|---|
| 00101 | 001 | Parotid×89 | < | 2380 | Absence of weight loss | 00102 | 80% | - |
| 00102 | 001 | ICD9 | = | 161 | Absence of weight loss | Presence of weight loss | 60% | 80% |
| 00103 | 002 | Parotid×70 | > | 1500 | Absence of weight loss | 00104 | 70% | - |
| 00104 | 002 | ICD9 | = | 170 | Absence of weight loss | Presence of weight loss | 90% | 60% |
| 00105 | 003 | Parotid×70 | > | 1400 | Absence of weight loss | 00106 | 70% | - |
| 00106 | 003 | ICD9 | = | 180 | Absence of weight loss | Presence of weight loss | 90% | 60% |

F I G. 3

| Patient ID | Patient name | Sex | Age |
|---|---|---|---|
| 1 | X | Male | 50 |
| 2 | Y | Male | 60 |
| 3 | Z | Female | 55 |

F I G. 4

| Treatment ID | Patient ID | ICD9 | LarynxX 75 | ParotidX 89 | ParotidX 70 | Presence/absence of weight loss |
|---|---|---|---|---|---|---|
| 1 | 1 | 170 | 1200 | 2560 | 1600 | Absence |
| 2 | 1 | 170 | 1000 | 2320 | 1700 | Presence |
| 3 | 2 | 161 | 1500 | 1800 | 1700 | Presence |

F I G. 5

| Clinician ID | Patient ID | Reference count |
|---|---|---|
| 1001 | 1 | 80 |
| 1001 | 2 | 55 |
| 1002 | 3 | 40 |
| ... | | |
| 1998 | 99 | 2 |
| 1999 | 100 | 1 |

F I G. 6

| Clinician ID | Treatment portion | Reference count |
|---|---|---|
| 1001 | Head and neck | 80 |
| 1001 | Chest | 55 |
| 1002 | Abdomen | 40 |
| ... | | |
| 1998 | Head and neck | 2 |
| 1999 | Chest | 1 |

F I G. 7

Example of mathematical model of model ID = 002 before update

| Model ID | Patient ID | Analysis result | Certainty factor | Actual treatment result | Accuracy index |
|---|---|---|---|---|---|
| 002 | 1 | Presence of weight loss | 80% | Absence of weight loss | False positive |
| 002 | 2 | Presence of weight loss | 80% | Presence of weight loss | True positive |
| 003 | 1 | Absence of weight loss | 70% | Absence of weight loss | True negative |
| 003 | 2 | Presence of weight loss | 90% | Presence of weight loss | True positive |

| Patient ID | Patient name | Age | Reference count | Actual treatment result | Mathematical model before update | Mathematical model after update | Certainty factor difference | Degree of clinical change |
|---|---|---|---|---|---|---|---|---|
| 1 | A | 50 | 80 | Presence of weight loss | Presence of weight loss (80%) | Absence of weight loss (40%) | -120% | Worsening |
| 2 | B | 60 | 55 | Presence of weight loss | Presence of weight loss (80%) | Presence of weight loss (80%) | 0% | No change |
| 3 | C | 55 | 40 | Presence of weight loss | Presence of weight loss (80%) | Absence of weight loss (80%) | -160% | Worsening |
| 4 | D | 80 | 35 | Absence of weight loss | Absence of weight loss (70%) | Absence of weight loss (80%) | 10% | Improvement |

FIG. 13

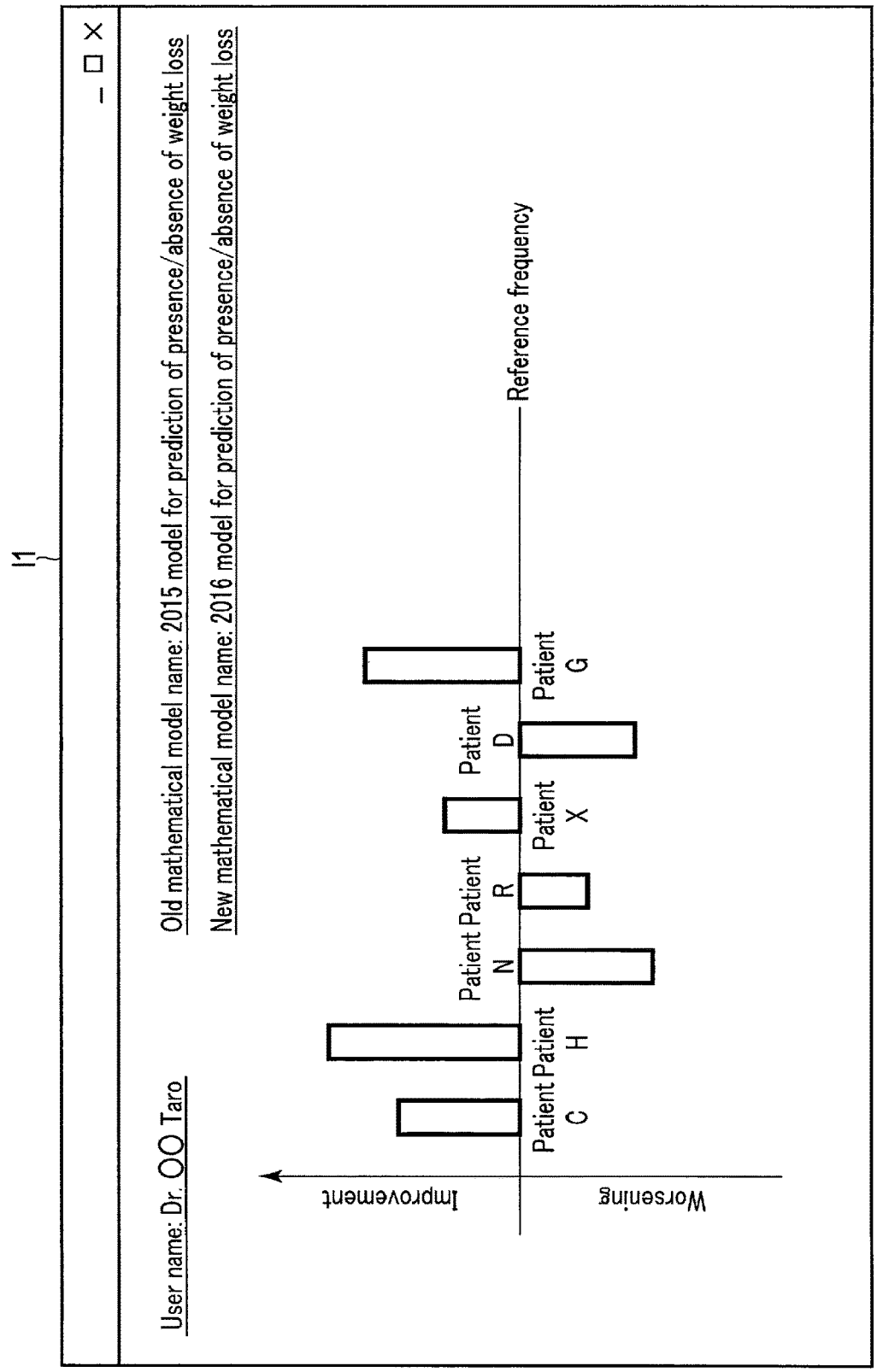
F I G. 14

User name: Dr. ○○ Taro

Assigned patient count: 34

Mathematical model name: Probability of cure of tumor

Certainty factor difference: difference equal to or more than 50% of probability of cure M2: Age Improved patient

| 60s | 70s | 80s |
|---|---|---|
| 11 | 2 | 2 |

Worsened patient

| 60s | 70s | 80s |
|---|---|---|
| 0 | 2 | 17 |

F I G. 17

RADIOTHERAPY PLANNING APPARATUS AND CLINICAL MODEL COMPARISON METHOD

CROSS-REFERENCE TO RELATED APPLICATIONS

This application is based upon and claims the benefit of priority from the Japanese Patent Application No. 2016-255330, filed Dec. 28, 2016, and the Japanese Patent Application No. 2017-248638, filed Dec. 26, 2017 the entire contents of both of which are incorporated herein by reference.

FIELD

Embodiments described herein relate generally to a radiotherapy planning apparatus and a clinical model comparison method.

BACKGROUND

In cancer radiotherapy, it is said that treatment progress such as the response (for example, the probability of cure after 3 months) of a cancer after irradiation and a side effect (for example, weight loss) influences the QOL (Quality Of Life) of a patient. Prediction of the treatment progress at the time of radiotherapy planning can support decision making so that a doctor makes a medical judgment (decides an action) effective for the QOL of a patient. If, for example, it is predicted that a cancer will not be reduced after 3 months, a doctor can make a medical judgment to reconsider a treatment plan. If it is predicted that weight loss will occur, a doctor can make a medical judgment to plan nutrition intervention such as gastrostomy. There are provided many tools for making it possible to construct/verify treatment progress prediction models. To accurately evaluate these prediction models, a user is required to be well versed in statistics.

BRIEF DESCRIPTION OF THE DRAWINGS

FIG. 2 is a table showing a basic model information table managed in a mathematical model database shown in FIG. 1;

FIG. 3 is a table showing a detailed model information table managed in the mathematical model database shown in FIG. 1;

FIG. 4 is a table showing a basic patient information table managed in a patient information database shown in FIG. 1;

FIG. 5 is a table showing a treatment result information table managed in the patient information database shown in FIG. 1;

FIG. 6 is a table showing a reference tendency information table that indicates reference tendency information for each patient and is managed in a reference tendency information database;

FIG. 7 is a table that indicates reference tendency information for each treatment portion and is managed in the reference tendency information database;

FIG. 13 is a table showing a comparison index (a certainty factor difference and the degree of a clinical change) calculated in step S3 of FIG. 8;

FIG. 14 is a view showing an example of a verification screen that is generated in step S6 of FIG. 8 and indicates the certainty factor difference and the degree of the clinical change between mathematical models before and after update for each of seven patients in descending order of a reference count;

FIG. 17 is a view showing a verification screen that is generated in step S6 of FIG. 8 from a viewpoint different from those in FIGS. 14 and 16.

DETAILED DESCRIPTION

Figure 1:
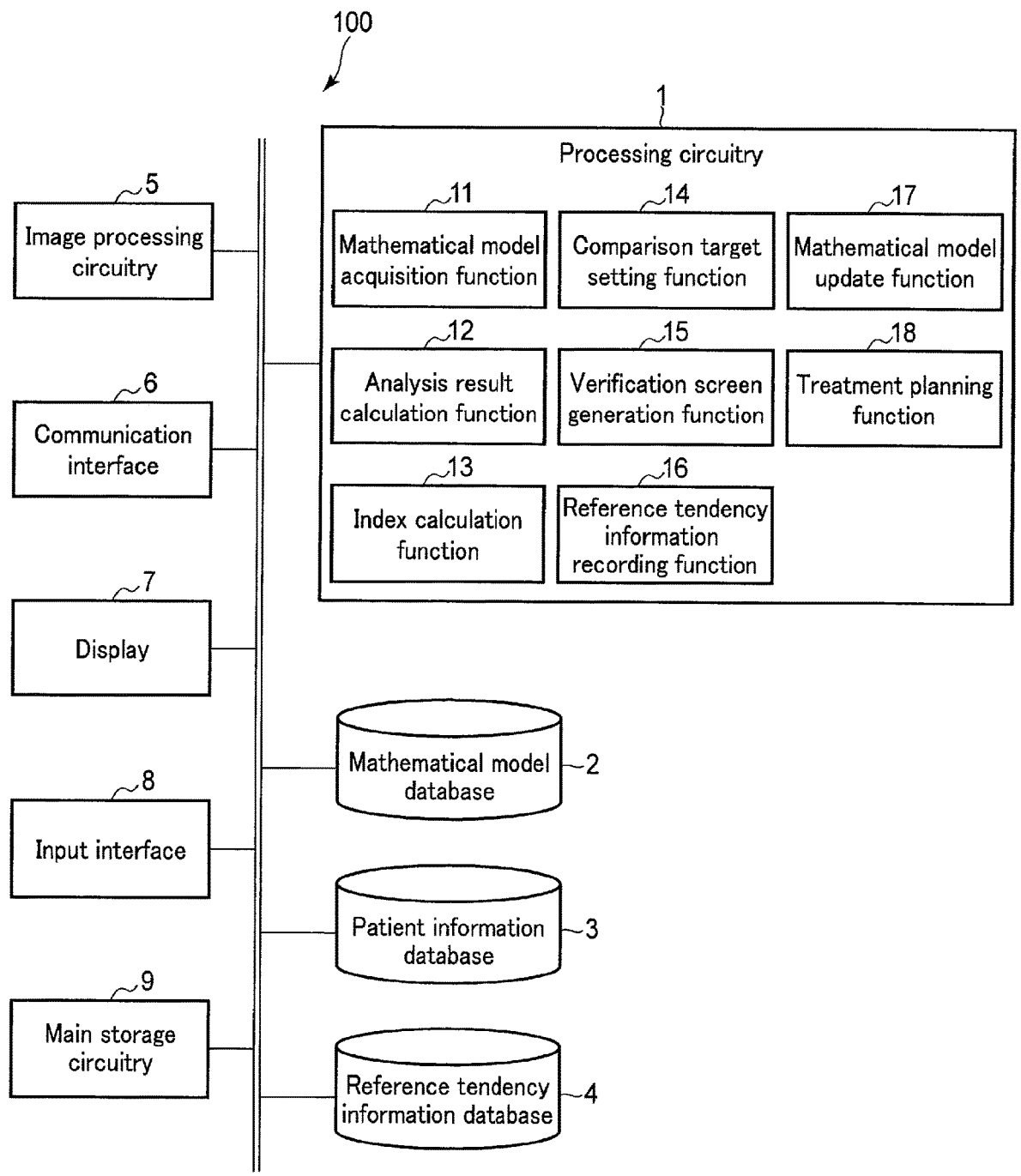
FIG. 1 is a block diagram showing the arrangement of a radiotherapy planning apparatus according to an embodiment.

A radiotherapy planning apparatus according to this embodiment includes processing circuitry and a display. The processing circuitry calculates, by applying patient information to each of a plurality of analysis models relating to clinical practice, analysis results based on the analysis models. The processing circuitry compares each of the analysis results with an actual clinical result relating to a comparison target patient, and generates evaluation information to evaluate a change between the analysis models. The display displays the evaluation information.

An analysis model according to the embodiment is a mathematical model which mathematically calculates the clinical result information based on patient information relating to the clinical practice of the patient. The mathematical model according to the embodiment includes a prediction model that predicts a future result based on actual patient information. The mathematical model according to the embodiment includes not only the prediction model that predicts a future result, but also a model that predicts (or analyzes) information which was not, is not or will not be measured. The clinical practice in this embodiment is medical practice including one of an examination, a diagnosis, a treatment and a follow-up.

The examination according to the embodiment indicates an examination using a blood test apparatus, an immunological test apparatus, and bio-instrumentation equipment, such as an electrocardiograph and a hemomanometer. For example, the mathematical model relating to the examination determines whether or not there is an abnormality in cardiac functions, using a electrocardiographic waveform and measurement results obtained by other bio-instrumentation equipment (for example, a blood-pressure value and blood component values), as input patient information. Even if an abnormality in the electrocardiographic waveform is not detected within an electrocardiographic waveform measurement period, the mathematical model according to the embodiment can predict a possibility of an abnormality in the electrocardiographic waveform after the electrocardiographic waveform measurement period.

The diagnosis according to the embodiment indicates a diagnosis using an X-ray computed tomography machine or a medical diagnostic imaging apparatus, such as an X-ray diagnosis apparatus, a magnetic resonance imaging apparatus, an ultrasonic diagnosis apparatus, or a nuclear medicine diagnosis apparatus. For example, the mathematical model relating to a diagnosis uses a medical image as input patient information, and outputs an image diagnosis result.

The treatment according to the embodiment indicates radiotherapy using a radiotherapy apparatus. A mathematical model relating to the radiotherapy will be described in detail later.

The follow-up according to the embodiment indicates a follow-up of a treatment portion after medical practice, such as an examination, a diagnosis, and a treatment, is provided there. For example, the mathematical model relating to the follow-up uses a medical image as input patient information, and outputs presence/absence of a relapse of a pathological abnormality, such as a cancer.

The mathematical models according to the embodiment will be described below referring to prediction models for predicting treatment progress of radiotherapy.

A radiotherapy planning apparatus and a clinical model comparison method according to this embodiment will be described below with reference to the accompanying drawings.

FIG. 1 is a block diagram showing the arrangement of a radiotherapy planning apparatus 100 according to this embodiment. As shown in FIG. 1, the radiotherapy planning apparatus 100 according to this embodiment includes processing circuitry 1, a mathematical model database 2, a patient information database 3, a reference tendency information database 4, image processing circuitry 5, a communication interface 6, a display 7, an input interface 8, and main storage circuitry 9. The processing circuitry 1, the mathematical model database 2, the patient information database 3, the reference tendency information database 4, the image processing circuitry 5, the communication interfaces 6, the display 7, the input interface 8, and the main storage circuitry 9 are communicably connected via a bus.

The processing circuitry 1 includes, as hardware resources, processors such as a CPU (Central Processing Unit) and a GPU (Graphics Processing Unit), and memories such as a ROM (Read Only Memory) and a RAM (Random Access Memory). The processing circuitry 1 implements a mathematical model acquisition function 11, an analysis result calculation function 12, an index calculation function 13, a comparison target setting function 14, a verification screen generation function 15, and a reference tendency information recording function 16 by executing a clinical model comparison program stored in the main storage circuitry 9. The mathematical model acquisition function 11, the analysis result calculation function 12, the index calculation function 13, the comparison target setting function 14, the verification screen generation function 15, and the reference tendency information recording function 16 correspond to modules of the clinical model comparison program, respectively. The processing circuitry 1 also implements a mathematical model update function 17 by executing a mathematical model update program stored in the main storage circuitry 9. In addition, the processing circuitry 1 implements a radiotherapy planning function 18 by executing a radiotherapy planning program stored in the main storage circuitry 9. Note that the processing circuitry 1 may be implemented by an ASIC (Application Specific Integrated Circuit), an FPGA (Field Programmable Gate Array), a CPLD (Complex Programmable Logic Device), or an SPLD (Simple Programmable Logic Device) capable of implementing the above functions.

In the mathematical model acquisition function 11, the processing circuitry 1 acquires, from the mathematical model database 2, a pair of mathematical models to be compared. The mathematical models according to this embodiment are mathematical models for predicting treatment progress of radiotherapy. The treatment progress to be predicted specifically includes the response of a tumor after radiation irradiation and the presence/absence of a side effect. The response of the tumor is indicated by, for example, the probability of cure of the tumor. The presence/absence of the side effect is indicated by, for example, the presence/absence of weight loss. The pair of mathematical models to be compared may be any mathematical models that can be compared. One of the mathematical models of the pair will be referred to as the first mathematical model hereinafter, and the other will be referred to as the second mathematical model hereinafter.

The mathematical model database 2 is a database for storing a plurality of mathematical models. More specifically, the mathematical model database 2 stores basic information (to be referred to as basic model information hereinafter) of each mathematical model, and detailed information (to be referred to as detailed model information hereinafter) of each mathematical model.

FIG. 2 is a table (to be referred to as a basic model information table hereinafter) of the basic model information. As shown in FIG. 2, the basic model information includes items of a model ID, algorithm, model name, current version, and old version. The model ID is an identifier assigned to the corresponding mathematical model. The algorithm is a kind of algorithm of the corresponding mathematical model. Any algorithm such as a decision tree or a regression tree is applicable as a mathematical model verification algorithm according to this embodiment. Another algorithm can be, for example, logistic regression or a neural network. The model name is the name of the corresponding mathematical model, or the name of a treatment progress item to be analyzed. Examples of the model name are weight loss for predicting the presence/absence of weight loss of a patient after radiation irradiation and tumor response for predicting the degree of reduction of a tumor after radiation irradiation. The current version is the current version of the corresponding mathematical model. The old version is the version of the corresponding mathematical model before update. For example, for a mathematical model of a model ID "002", the algorithm is "decision tree", the model name is "weight loss", the current version is "2.0", and the old version is "1.0". Note that a mathematical model having "–" as the old version such as a mathematical model of a model ID "001" or "004" indicates a mathematical model having a current version "1.0", that is, a mathematical model of an initial version. The basic model information table is managed in the mathematical model database 2.

FIG. 3 is a table (to be referred to as a detailed model information table hereinafter) of the detailed model information. As shown in FIG. 3, the detailed model information includes items of a parameter ID, model ID, parameter name, operator, value, false branch, true branch, the certainty factor of the true branch, and the certainty factor of the false branch. Note that the detailed model information shown in FIG. 3 is an example of detailed information of a mathematical model using the decision tree. Note that the detailed model information table is applicable not only to a mathematical model using the decision tree but also to a mathematical model using the logistic regression or neural network, and has a table structure corresponding to the mathematical model.

The parameter ID is an identifier assigned to each of parameters forming the corresponding mathematical model. The parameter name is the name of the corresponding parameter. The operator is an operator forming the conditional expression of a branch, and defines the relationship between a parameter value and a condition value. More specifically, examples of the operator are "<" indicating that the parameter value is smaller than the condition value, ">" indicating that the parameter value is larger than the condition value, and "=" indicating that the parameter value is equal to the condition value. The condition value is a value forming the conditional expression of the branch, and is to be compared with the parameter value. The false branch is a next node to which the process transits when the conditional expression of the branch is not satisfied. The next node indicates a next branch or a false leaf that outputs an analysis result. The true branch is a next node to which the process transits when the conditional expression of the branch is satisfied. The next node indicates a next branch or a true leaf that outputs an analysis result. The certainty factor of the false branch indicates a certainty factor for the analysis result of the false branch. The certainty factor of the true branch indicates a certainty factor for the analysis result of the true branch. In this embodiment, the certainty factors are a kind of analysis result. Note that the certainty factors are not essential items. If, for example, the analysis result is a numerical value such as the probability of cure, the certainty factors need not be set.

For example, assume that for a parameter of a parameter ID "00102", the model ID is "001", the parameter name is "ICD9", the operator is "=", the condition value is "161", the false branch is "absence of weight loss", the true branch is "presence of weight loss", the certainty factor of the false branch is "60%", and the certainty factor of the true branch is "80%". Note that a parameter having "−" as the certainty factor of the true branch such as a parameter of a parameter ID "00101" or "00103" indicates that it is not at a stage where an analysis result can be calculated since there exists a next branch. The detailed model information table is managed in the mathematical model database 2.

As shown in FIG. 2, the mathematical model according to this embodiment can use various algorithms such as the decision tree and regression tree. For example, if the algorithm is the decision tree, each mathematical model is formed by a plurality of conditional expressions connected in the form of a tree diagram, as shown in FIG. 3. Each conditional expression is formed by the parameter, operator, and condition value. Each conditional expression defines the relationship that is described by the operator and is to be satisfied between the parameter value and the condition value to transit to the true branch. If the conditional expression is satisfied, the process transits to the true branch; otherwise, the process transits to the false branch.

In the analysis result calculation function 12, the processing circuitry 1 applies the first mathematical model and the second mathematical model to each of pieces of patient information of a plurality of patients, thereby calculating the first analysis result based on the first mathematical model and the second analysis result based on the second mathematical model for each of the plurality of patients. The patient information is stored in the patient information database 3.

The patient information database 3 is a database for storing pieces of patient information of a plurality of patients. The patient information includes basic patient information and treatment result information. The basic patient information is basic information for specifying a patient. The treatment result information is information about the result of a treatment actually applied to the patient.

FIG. 4 is a table (to be referred to as a basic patient information table hereinafter) of the basic patient information. As shown in FIG. 4, the basic patient information includes items of a patient ID, patient name, sex, and age. The patient ID is an identifier assigned to the corresponding patient. The patient name is the name of the corresponding patient. The sex is the sex of the corresponding patient. The age is the age of the corresponding patient. For example, for a patient of a patient ID "1", the patient name is "X", the sex is "male", and the age is "50". The basic patient information table is managed in the patient information database 3.

FIG. 5 is a table (to be referred to as a treatment result information table) of the treatment result information. As shown in FIG. 5, the treatment result information includes items of a treatment ID, patient ID, ICD9, LarynxX75, ParotidX89, ParotidX70, and the presence/absence of weight loss. The treatment ID is an identifier assigned to a treatment applied to the corresponding patient. The patient ID is an identifier assigned to the corresponding patient. ICD9 is one of parameters indicating the disease name and diagnosis result of the corresponding patient. Each of LarynxX75, ParotidX89, and ParotidX70 is one of irradiation parameters in radiotherapy. The presence/absence of weight loss is one of parameters for evaluating the progress of the treatment. The items of ICD9, LarynxX75, ParotidX89, ParotidX70, and the presence/absence of weight loss are associated with a treatment result actually measured after the treatment. The treatment result information table is managed in the patient information database 3.

In the index calculation function 13, for each of the plurality of patients, the processing circuitry 1 calculates the first accuracy index indicating the accuracy of the first analysis result based on the actual treatment result and the first analysis result, calculates the second accuracy index indicating the accuracy of the second analysis result based on the actual treatment result and the second analysis result, and calculates a comparison index indicating comparison between the first and second analysis results. The treatment result information stored in the patient information database 3 is used as the actual treatment result. The first and second accuracy indices are the same kind of accuracy indices to evaluate the first and second analysis results.

In the comparison target setting function 14, the processing circuitry 1 sets comparison target patients from the plurality of patients. The comparison target patients may be set based on reference tendency information (to be described later), or arbitrarily set by the user via the input interface 8.

In the reference tendency information recording function 16, the processing circuitry 1 records reference tendency information in the reference tendency information database 4. The reference tendency information is information about a tendency of reference to medical information such as patient information and medical images by a medical staff such as a doctor or technician in a usual medical treatment process (workflow) of radiotherapy. The reference tendency information is recorded for each subject (to be referred to as a reference subject hereinafter), such as each department or occupation, that refers to medical information, each object (to be referred to as a reference object hereinafter), such as each patient or treatment portion, of medical information, each period (to be referred to as a reference period hereinafter) during which medical information is referred to, or each treatment apparatus (to be referred to as a reference treatment apparatus hereinafter) used for a treatment associated with medical information. Note that examples of the occupation as the reference subject are a doctor, technician, and nurse. Examples of the treatment apparatus are an IGRT (Image Guided Radiotherapy) apparatus and an IMRT (Intensity Modulated Radiation Therapy) apparatus. The treatment apparatus is not limited to a large-scale apparatus, and may be a small device used for brachytherapy.

The reference tendency information database 4 is a database for storing the reference tendency information. An example of the reference tendency information is a reference count for each reference subject, each reference object, each reference period, or each reference treatment apparatus.

FIG. 6 is a table (to be referred to as a reference tendency information table hereinafter) of the reference tendency information for each patient. As shown in FIG. 6, the reference tendency information for each patient includes items of a clinician ID, patient ID, and reference count. The clinician ID is an identifier assigned to a clinician as a reference subject in charge of the corresponding patient. The patient ID is an identifier assigned to the corresponding patient. The reference count is the number of times the clinician refers to medical information of the corresponding patient. For example, for a clinician of a clinician ID "1001", the reference count for medical information of the patient of the patient ID "1" is "80".

FIG. 7 is a table showing a reference tendency information table for each treatment portion. As shown in FIG. 7, the reference tendency information for each treatment portion includes items of a clinician ID, treatment portion, and reference count. The clinician ID is an identifier assigned to a clinician in charge of a treatment for the treatment portion as a reference object. The treatment portion is the name of the treatment portion. The reference count is the number of times the clinician refers to medical information about the treatment portion. For example, for a clinician of a clinician ID "1001", the reference count for medical information of a treatment portion "head and neck" is "80".

In the verification screen generation function 15, the processing circuitry 1 generates evaluation information to evaluate a clinical change between the first and second mathematical models. The evaluation information indicates, for example, a degree of improvement or worsening of the second mathematical model with reference to the first mathematical model. As another example, the evaluation information may indicate determination whether the second mathematical model is improved or worsened relative to the first mathematical model. More specifically, in the verification screen generation function 15, the processing circuitry 1 calculates a clinical change between the first and second prediction results with reference to the actual treatment result for each of the comparison target patients set by the verification target setting function 14. The processing circuitry 1 generates a verification screen showing the tendency of the clinical change. More specifically, the processing circuitry 1 generates a verification screen schematically showing at least one of the first and second accuracy indices or comparison index with respect to the comparison target patient.

In the mathematical model update function 17, the processing circuitry 1 updates the mathematical model. Update of the mathematical model indicates change, addition, and deletion of intrinsic parameters forming the mathematical model. The intrinsic parameters according to this embodiment correspond to the values of the items of the detailed information forming the mathematical model. If, for example, the algorithm is the decision tree, update of the mathematical model indicates change, addition, and deletion of at least one of the operator, condition value, or branch destination, which form the mathematical model.

In the radiotherapy planning function 18, the processing circuitry 1 creates a treatment plan for the corresponding patient based on a treatment plan image and like generated by a medical image diagnostic apparatus and the like. The items of the treatment plan include, for example, a treatment portion, the dose distribution of radiation, a radiation irradiation method, and a radiotherapy condition. Information about the treatment plan is transmitted to a radiotherapy apparatus. The radiotherapy apparatus performs radiation irradiation in accordance with the treatment plan to kill or reduce a tumor of the patient.

The image processing circuitry 5 includes, as hardware resources, processors such as a CPU and a GPU, and memories such as a ROM and a RAM. The image processing circuitry 5 performs various image processes for the treatment plan image. For example, the image processing circuitry 5 generates a 2D medical image for display by performing, for a 3D treatment plan image, 3D image processing such as volume rendering, surface volume rendering, image value projection processing, MPR (Multi-Planer Reconstruction) processing, and CPR (Curved MPR) processing. Note that the image processing circuitry 5 may be implemented by an ASIC, FPGA, CPLD, or SPLD capable of implementing the above image processes.

The communication interface 6 includes a communication interface for performing, via wired or wireless connection (not shown), data communication with a radiotherapy apparatus, PACS (Picture Archiving and Communication System), HIS (Hospital Information System), RIS (Radiology Information System), OIS (Oncology Information System), or the like.

The display 7 displays various kinds of information such as the verification screen generated by the verification screen generation function 15. More specifically, for example, a CRT display, liquid crystal display, organic EL display, LED display, plasma display, or any other display known in this technical field is appropriately usable as the display 7.

The input interface 8 specifically includes an input device and input interface circuitry. The input device accepts various commands from the user. A keyboard, a mouse, various switches, and the like are usable as the input device. The input interface circuitry supplies, to the processing circuitry 1, via the bus, an output signal from the input device.

The main storage circuitry 9 is a storage device such as an HDD (Hard Disk Drive), SSD (Solid State Drive), or integrated circuit storage device for storing various kinds of information. For example, the main storage circuitry 9 stores the clinical model comparison program, model update program, and radiotherapy planning program. The main storage circuitry 9 as hardware may be a driving device that reads/writes various kinds of information from/in a portable storage medium such as a CD-ROM drive, DVD drive, or flash memory.

An example of the operation of the radiotherapy planning apparatus 100 by executing the clinical model comparison program according to this embodiment will be described next. The radiotherapy planning apparatus 100 executes the clinical model comparison program for comparing and verifying two mathematical models of the same kind. For example, mathematical models before and after update by the mathematical model update function 17 are set as the two mathematical models of the same kind to be compared and verified. The mathematical models of the same kind indicate mathematical models whose algorithms are the same but whose intrinsic parameters are different. For example, if the algorithm is the decision tree, the mathematical models of the same kind indicate mathematical models having different operators, condition values, and branch destinations. The mathematical models of the same kind may be mathematical models whose algorithms are different but whose analysis targets are the same. For example, a mathematical model for predicting weight loss by the decision tree and a mathematical model for predicting weight loss by the regression tree can be comparison targets as the mathematical models of the same kind.

The two mathematical models to be compared according to this embodiment are not limited to the mathematical models before and after update. If two mathematical model use subjects such as hospitals, departments, or medical staffs use different intrinsic parameters, mathematical models for the respective use subjects are set as the two mathematical models of the same kind to be compared. For example, a mathematical model used in hospital A and a mathematical model used in hospital B may be set as mathematical models to be compared.

Figure 8:
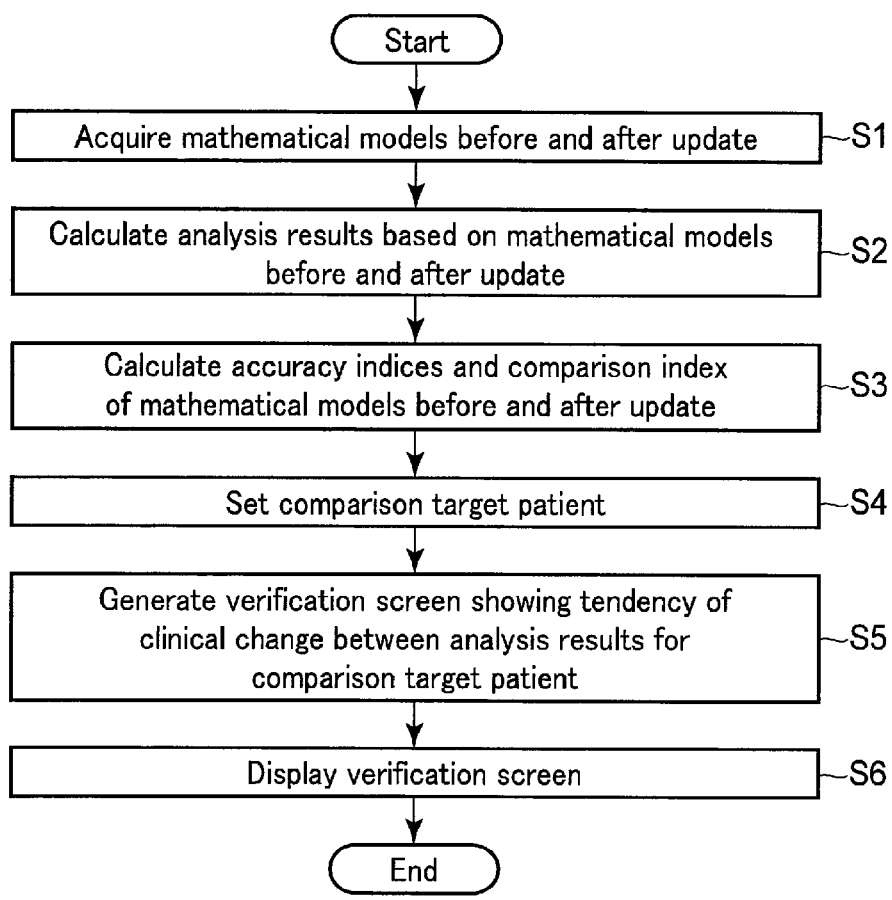
FIG. 8 is a flowchart illustrating a model comparison executed by processing circuitry shown in FIG. 1 in accordance with a clinical model comparison program.

FIG. 8 is a flowchart illustrating the procedure of mathematical model comparison executed by the processing circuitry 1 in accordance with the clinical model comparison program. The processing circuitry 1 starts a mathematical model comparison when a start instruction is automatically input or input by the user via the input interface 8 after completion of update of a mathematical model by the mathematical model update function 17. Note that if update of a mathematical model is complete, the mathematical model update function 17 supplies an update completion notification to the mathematical model acquisition function 11. Note that the update completion notification may include information of the model ID of the mathematical model for which update is complete.

As shown in FIG. 8, the processing circuitry 1 executes the mathematical model acquisition function 11 (step S1). In step S1, the processing circuitry 1 acquires mathematical models before and after update. The processing in step S1 will be described in detail below.

In step S1, the processing circuitry 1 acquires detailed model information of a mathematical model after update from the mathematical model database 2. More specifically, the processing circuitry 1 searches the detailed model information table shown in FIG. 3 using, as a search keyword, the model ID of the mathematical model after update, and specifies the old version number of a mathematical model before update. For example, if the model ID is "003", pieces of detailed model information of parameter IDs "00105" and "00106" are specified.

Next, the processing circuitry 1 acquires detailed information of the mathematical model before update from the mathematical model database 2. More specifically, the processing circuitry 1 searches the basic model information table shown in FIG. 2 using, as a search keyword, the model ID of the mathematical model after update, and specifies the old version number and model ID of the mathematical model before update. For example, if the model ID is "003", an old version number "2.0" and a model ID "002" are specified. Next, the processing circuitry 1 searches the detailed model information table shown in FIG. 3 using, as a search keyword, the model ID of the mathematical model before update, and specifies detailed information of the mathematical model before update. If the model ID is "002", pieces of detailed information of parameter IDs "00103" and "00104" are specified. Note that, for example, two mathematical models having the same old version number may be specified as mathematical models before update. For example, if the mathematical model of the current version "2.1" and the mathematical model of the current version "3.0" have an old version number "2.0", the mathematical model of the current version "2.1" is specified as a mathematical model before update, and the mathematical model of the current version "3.0" is specified as a mathematical model after update.

The processing circuitry 1 reproduces a mathematical model before update based on the acquired detailed information of the mathematical model before update, and constructs a mathematical model after update based on the acquired detailed information of the mathematical model after update.

Figure 9:
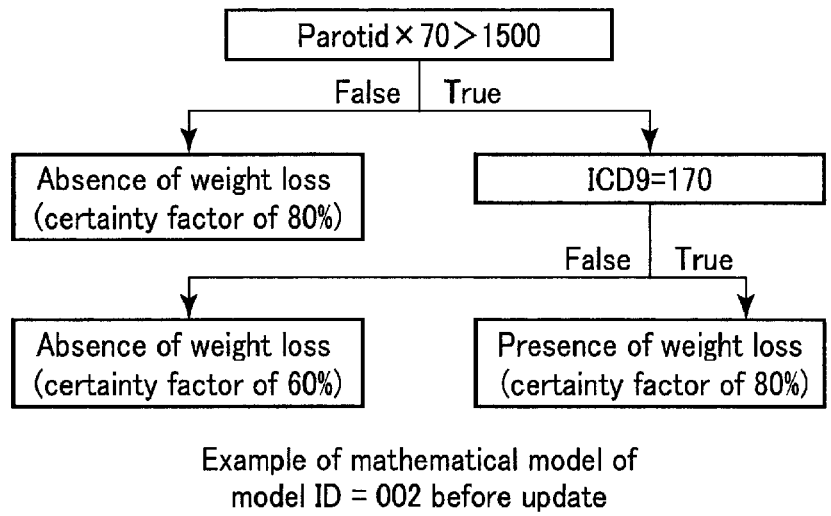
FIG. 9 is a view showing a mathematical model of a model ID "002" in FIGS. 2 and 3, that is constructed in step S1 of FIG. 8.

More specifically, an example of constructing the mathematical model of the model ID "002" as a mathematical model before update will be described. FIG. 9 is a view showing the mathematical model of the model ID "002" shown in FIGS. 2 and 3. The processing circuitry 1 searches the detailed information table shown in FIG. 3 using the model ID "002" as a search keyword, and specifies detailed information of the mathematical model of the model ID "002". For example, in FIG. 3, the pieces of detailed information of the parameter IDs "00103" and "00104" are specified.

The processing circuitry 1 specifies, as the parameter ID of the root node of the decision tree, a parameter ID included in none of the false branches and true branches from the plurality of parameter IDs of the specified mathematical model before update. For example, in the above example, the parameter ID "00104" of the parameter IDs "00103" and "00104" is included in the true branch of the parameter ID "00103" and thus does not correspond to the root node. The parameter ID "00103" is included in none of the true branches and false branches of the parameter IDs "00103" and "00104", and is thus specified as the parameter ID of the root node.

The processing circuitry 1 acquires the parameter name, operator, and condition value of the specified root node, and decides a conditional expression for the root node of the decision tree based on the acquired parameter name, operator, and condition value. For example, if the parameter ID of the root node is "00103", the parameter name "ParotidX70", operator ">", and value "1500" are specified, and thus "ParotidX70>1500" is decided as a conditional expression.

The processing circuitry 1 specifies the values of the false and true branches of the specified root node. The processing circuitry 1 determines the types of the specified values of the false and true branches. If the value of the false branch is an analysis result, the processing circuitry 1 sets the false branch as an end terminal (false leaf), and sets the analysis result as an output from the false branch. At this time, if the certainty factor of the false branch is input, the processing circuitry 1 also sets the certainty factor of the false branch as the analysis result of the false branch. Similarly, with respect to the true branch, the analysis result and the certainty factor of the true branch are set for the end terminal (true leaf) of the true branch. If the specified value is a parameter ID, the processing circuitry 1 sets the intrinsic parameters of the parameter ID in the next branch. With respect to the set next branch, the same step as that described above is executed to decide a conditional expression and specify the values of the false and true branches. For example, if the parameter ID of the root node is "00103", "absence of weight loss" as the analysis result and "70%" as the certainty factor of the false branch are set as an output for the false branch, and the next branch "00104" is set for the true branch.

The processing circuitry 1 executes the above processing until conditional expressions are decided and the values of the false and true branches are specified for all the branches. If the above processing is performed for all the branches, construction of the mathematical model ends. Note that a mathematical model after update can be constructed by the same process as that for the mathematical model before update.

After step S1 is performed, the processing circuitry 1 executes the analysis result calculation function 12 (step S2). In step S2, the processing circuitry 1 calculates an analysis result (to be referred to as a pre-update analysis result hereinafter) based on the mathematical model before update and an analysis result (to be referred to as a post-update analysis result hereinafter) based on the mathematical model after update using each of the pieces of patient information of the plurality of patients as calculation targets, that have been acquired from the patient information database 3. As the plurality of patients as calculation targets, all the patients stored in the patient information database 3 or a plurality of patients assigned to the user may be set. Calculation of analysis results will be described in detail below.

First, the processing circuitry 1 acquires a patient list from the patient information database 3. The patient list is, for example, the treatment result information table stored in the patient information database 3. Next, the processing circuitry 1 extracts treatment result information of an arbitrary patient from the patient list, and acquires, from the extracted treatment result information, the actual measured values of the parameters of the patient used by the mathematical models before and after update. For example, since the mathematical model of the model ID "002" uses ICD9 and ParotidX70, an actual measured value "170" of ICD9, an actual measured value "1600" of ParotidX70, and the like are acquired for a record of the patient ID "1" of a treatment ID "1" in FIG. 5. The processing circuitry 1 calculates the analysis results of the mathematical models based on the acquired actual measured values of the parameters.

Figure 10:
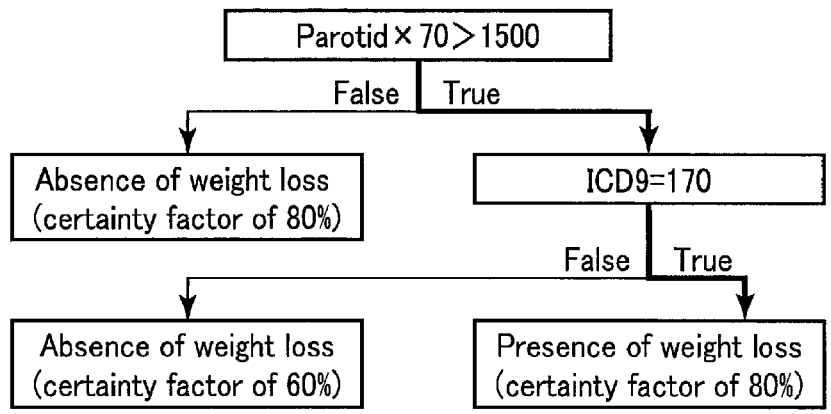
FIG. 10 is a view schematically showing an analysis result calculation step based on a mathematical model before update corresponding to the model ID "2" in FIG. 3 using treatment result information of a patient ID "1" of a treatment ID "1" in FIG. 5.
Figures 11, 12:
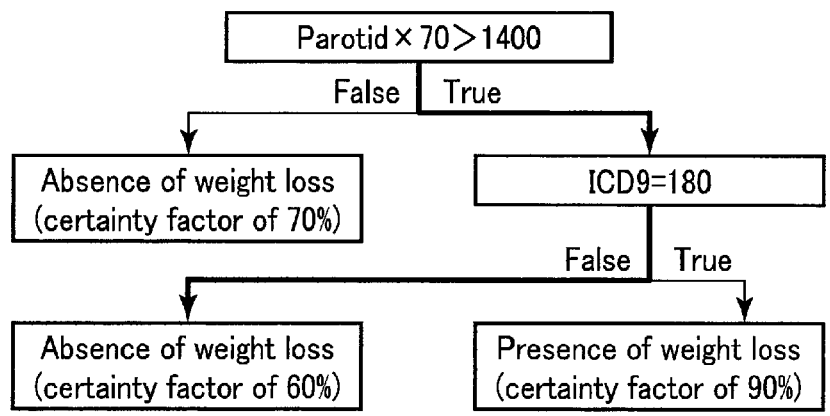
FIG. 11 is a view schematically showing an analysis result calculation step based on a mathematical model before update corresponding to a model ID "3" in FIG. 3 using the treatment result information of the patient ID "1" of the treatment ID "1" in FIG. 5.
FIG. 12 is a table showing a result of calculating accuracy indices in step S3 of FIG. 8.

FIG. 10 is a view schematically showing the analysis result calculation step based on the mathematical model before update corresponding to the model ID "2" shown in FIG. 3 using the treatment result information of the patient ID "1" of the treatment ID "1" shown in FIG. 5. FIG. 11 is a view schematically showing a step of calculating a pre-update analysis result corresponding to a model ID "3" shown in FIG. 3 using the treatment result information of the patient ID "1" of the treatment ID "1" shown in FIG. 5. As shown in FIG. 10, for the mathematical model before update, it is determined whether Parotidx70 is larger than 1500. As shown in FIG. 5, for the patient ID "1" of the treatment ID "1", Parotidx70 is "1600". Since, therefore, Parotidx70 is larger than 1500, the process transits to the true branch. As shown in FIG. 10, in the next true branch, it is determined whether ICD9 is equal to 170. As shown in FIG. 5, for the patient ID "1" of the treatment ID "1", ICD9 is "170". Since, therefore, ICD9 is equal to 170, the process transits to the true branch. Consequently, the pre-update analysis result is "presence of weight loss" and the certainty factor is "80%".

For the mathematical model after update, as shown in FIG. 11, it is determined whether ParotidX70 is larger than 1400. As shown in FIG. 5, for the patient ID "1" of the treatment ID "1", Parotidx70 is "1600". Since, therefore, Parotidx70 is larger than 1400, the process transits to the true branch. As shown in FIG. 11, in the next true branch, it is determined whether ICD9 is equal to 180. As shown in FIG. 5, for the patient ID "1" of the treatment ID "1", ICD9 is "170". Since, therefore, ICD9 is not equal to 180, the process transits to the false branch. Consequently, the post-update analysis result is "absence of weight loss" and the certainty factor is "60%".

After step S2 is performed, the processing circuitry 1 executes the index calculation function 13 (step S3). In step S3, the processing circuitry 1 calculates an accuracy index based on the pre-update analysis result, an accuracy index based on the post-update analysis result, and a comparison index indicating comparison between the accuracy index based on the mathematical model before update and that based on the mathematical model after update.

More specifically, the processing circuitry 1 acquires the information and analysis result of the mathematical model before update, and the information and analysis result of the mathematical model after update, which have been calculated by the analysis result calculation function 12, and calculation target patient information. The processing circuitry 1 acquires actual treatment result information of the calculation target patient information from the patient information database 3. For example, for the patient of the patient ID "1" of the treatment ID "1" shown in FIG. 5, the treatment result "absence of weight loss" is acquired. The processing circuitry 1 compares the analysis result with the treatment result to calculate an accuracy index indicating the accuracy of the prediction. The accuracy index is calculated for each of the mathematical models before and after update.

FIG. 12 is a table showing accuracy index calculation results. As shown in FIG. 12, the accuracy indices are classified into, for example, a true positive, a false positive, a true negative, and a false negative. The true positive is calculated when the analysis result is "presence of weight loss" and the treatment result is "presence of weight loss". The false positive is calculated when the analysis result is "presence of weight loss" and the treatment result is "absence of weight loss". The true negative is calculated when the analysis result is "absence of weight loss" and the treatment result is "absence of weight loss". The false negative is calculated when the analysis result is "absence of weight loss" and the treatment result is "presence of weight loss". For example, for the patient ID "1", the analysis result of the mathematical model of the model ID "002" is "presence of weight loss" but the treatment result is "absence of weight loss". Therefore, the accuracy index is the "false positive". Note that the accuracy index is not limited to them, and any index may be used as long as it can indicate the degree of matching between the analysis result and the treatment result.

The processing circuitry 1 calculates a comparison index indicating comparison between the pre-update analysis result and the post-update analysis result. The comparison index indicates a tendency of a change between the degrees of matching of the pre-update analysis result and post-update analysis result with respect to the actual treatment result when the mathematical model before update is updated to the mathematical model after update.

FIG. 13 is a table showing the comparison index. As shown in FIG. 13, the processing circuitry 1 calculates a degree of a clinical change and a certainty factor difference as the comparison index. The definitions of the degree of the clinical change and the certainty factor difference are different between mathematical models for predicting the presence/absence of a side effect and mathematical models for predicting the numerical values of the treatment progress parameters. The degree of the clinical change and the certainty factor difference for the mathematical models for predicting the presence/absence of the side effect will be described.

The degree of the clinical change indicates the classification of the tendency of the clinical change of the post-update analysis result with respect to the pre-update analysis result. More specifically, the degree of the clinical change is decided based on whether the post-update analysis result has been clinically improved or worsened, or has not been changed with respect to the pre-update analysis result. The certainty factor difference is defined as the difference between the certainty factor of the pre-update analysis result and that of the post-update analysis result. More specifically, the certainty factor difference is defined as a value (subtraction value) obtained by subtracting the certainty factor of the pre-update analysis result from that of the post-update analysis result. The degree of the clinical change is classified into "improvement" when the subtraction value is "+", "worsening" when the subtraction value is "−", or "no change" when the subtraction value is 0.

The processing circuitry 1 calculates the certainty factor difference based on the actual treatment result, the pre-update analysis result, and the post-update analysis result. More specifically, for each of the mathematical models before and after updates, the processing circuitry 1 determines whether the actual treatment result matches the analysis result. If the actual treatment result matches the analysis result, the processing circuitry 1 sets the sign of the certainty factor to "+"; otherwise, the processing circuitry 1 sets the sign of the certainty factor to "−". Then, the processing circuitry 1 calculates the certainty factor difference by subtracting the signed certainty factor of the pre-update analysis result from that of the post-update analysis result. The processing circuitry 1 specifies the sign and value of the certainty factor difference. If the sign of the certainty factor difference is "−", the degree of the clinical change is set to "worsening". If the sign of the certainty factor difference is "+", the degree of the clinical change is set to "improvement". If the certainty factor difference is 0, the degree of the clinical change is set to "no change".

For example, if, like a patient "A", the treatment result is "presence of weight loss", the pre-update analysis result is "presence of weight loss (certainty factor: 80%)", and the post-update analysis result is "absence of weight loss (certainty factor: 40%)", the certainty factor difference is (−40)−80=−120, and the degree of the clinical change is "worsening". If, like a patient "D", the treatment result is "absence of weight loss", the pre-update analysis result is "absence of weight loss (certainty factor: 70%)", and the post-update analysis result is "absence of weight loss (certainty factor: 80%)", the certainty factor difference is (80)−70=10, and the degree of the clinical change is "improvement".

The degree of the clinical change and the certainty factor difference for the mathematical models for predicting the numerical values of the treatment progress parameters will be described next. As the mathematical models for predicting the numerical values of the treatment progress parameters, the mathematical models for the probability of cure of the tumor are exemplified. The degree of the clinical change is decided based on whether the post-update analysis result has been clinically improved or worsened, or has not been changed with respect to the pre-update prediction result. The certainty factor difference is defined as the difference between the pre-update analysis result (numerical value) and the post-update analysis result (numerical value). The degree of the clinical change is classified into "improvement" when the subtraction value is "+", "worsening" when the subtraction value is "−", or "no change" when the subtraction value is 0.

The processing circuitry 1 calculates the certainty factor difference based on the actual treatment result, the pre-update analysis result, and the post-update analysis result. If the treatment result is "cured", the sign of the probability of cure as the analysis result is set to "+". If the treatment result is "not cured", the sign of the probability of cure as the analysis result is set to "−". For example, if the treatment result is "cured", the pre-update analysis result is "probability of cure: 10%", and the post-update analysis result is "probability of cure: 95%", the certainty factor difference is (95)−10=85, and thus the degree of the clinical change is "improvement". If the treatment result is "not cured", the pre-update analysis result is "probability of cure: 80%", and the post-update analysis result is "probability of cure: 20%", the certainty factor difference is (−20)−(−80)=60, and thus the degree of clinical change is "improvement".

After step S3 is performed, the processing circuitry 1 executes the comparison target setting function 14 (step S4). In step S4, the processing circuitry 1 sets comparison target patients from the plurality of patients based on the reference tendency information stored in the reference tendency information database 4.

If, for example, the reference count for each patient in FIG. 6 is stored as the reference tendency information, the processing circuitry 1 sets, as comparison targets, 10 patients in descending order of the reference count. Note that the comparison targets are not limited to the 10 patients from the top, and patients of any ordinal numbers from the top may be set. The present invention is not limited to a predetermined number of patients from the top, and the predetermined number of patients from the bottom may be set.

As described above, the reference tendency information is recorded by the reference tendency information recording function 16 of the processing circuitry 1. More specifically, if a reference subject such as a doctor uses the radiotherapy apparatus, PACS, HIS, RIS, or OIS, the processing circuitry 1 acquires the ID of the reference subject. The processing circuitry 1 detects an event (to be referred to as a reference event hereinafter) of referring to (accessing) medical information of a patient by the reference subject. For example, the processing circuitry 1 detects, as a reference event, via the input interface 8 or the like, transition of the screen of a user interface or an input operation for referring to medical information. Based on the ID of the reference subject and the ID of the patient as the reference object, the processing circuitry 1 increases the reference count for a combination of the reference subject and reference object.

Note that a medical treatment process of radiotherapy at the time of reference may be included as the reference tendency information. In this case, the processing circuitry 1 acquires the medical treatment process of radiotherapy at the time of reference from the radiotherapy apparatus, PACS, HIS, RIS, or OIS along with detection of the reference event. Examples of the medical treatment process are creation of a treatment plan, replanning of the treatment plan, and follow-up. The processing circuitry 1 increases the reference count in the acquired medical treatment process. In this case, when setting comparison target patients, it is possible to consider the reference counts for each medical treatment process. For example, 10 patients in descending order of the reference count at the time of follow-up can be set as comparison target patients.

The comparison target patients are not limited to some of the plurality of patients for which the accuracy indices have been calculated. That is, all the plurality of patients for which the accuracy indices have been calculated may be set as comparison targets. In this case, the processing circuitry 1 automatically sets, as comparison targets, all the plurality of patients for which the accuracy indices have been calculated, without using the reference tendency information. Alternatively, arbitrary patients designated by the user via the input circuitry 8 among the plurality of patients for which the accuracy indices have been calculated may be set as comparison target patients.

After step S4 is performed, the processing circuitry 1 executes the verification screen generation function 15 (step S5). In step S5, the processing circuitry 1 generates a verification screen showing the tendency of the clinical change between the pre-update analysis result and the post-update analysis result.

After step S5 is performed, the processing circuitry 1 causes the display 7 to execute display processing (step S6). In step S6, the display 7 displays the verification screen generated by the verification screen generation function 15.

The verification screen generation processing in step S5 and the verification screen display processing in step S6 will be described in detail below by exemplifying a case in which a predetermined number of patients in descending order of the reference count are set as comparison targets.

The processing circuitry 1 generates a verification screen based on at least one of the pre-update analysis result, the post-update analysis result, the accuracy index based on the pre-update analysis result, the accuracy index based on the post-update analysis result, or the comparison index, all of which are associated with each comparison target patient. For example, the processing circuitry 1 generates, as a verification screen, a chart (graph) showing the certainty factor differences and the degrees of the clinical changes for the mathematical models before and after update, which are associated with the predetermined number of patients in descending order of the reference count.

FIG. 14 is a view showing an example of a verification screen I1 showing the certainty factor differences and the degrees of the clinical changes for the mathematical models before and after update, which are associated with seven patients in descending order of the reference count. As shown in FIG. 14, the mathematical model before update is a 2015 model for prediction of the presence/absence of weight loss, and the mathematical model after update is a 2016 model for prediction of the presence/absence of weight loss. The user of mathematical model verification processing is Dr. ○○ Taro. The comparison target patients are seven patients in descending order of the reference count by Dr. ○○ Taro.

As shown in FIG. 14, in the verification screen I1, the ordinate is defined as the certainty factor difference and the abscissa is defined as the reference count. The + range of the certainty factor difference is categorized as "improvement" of the degree of the clinical change, and the − range of the certainty factor difference is categorized as "worsening" of the degree of the clinical change. The verification screen I1 visually shows the certainty factor difference and the degree of the clinical change for each patient by the length and direction of each bar. That is, the length of each bar represents the absolute value of the certainty factor difference, and the direction of each bar represents the degree of the clinical change. The display 7 displays the verification screen I1, thereby making it possible to clearly present information indicating whether the analysis result has been improved or worsened before and after update of the mathematical model and information indicating the degree of improvement or worsening. Furthermore, the bars of the patients are arranged so that the bar closer to the origin of the graph indicates a larger reference count. In FIG. 14, the patient C has the largest reference count. By arraying the bars of the patients in accordance with the reference counts, the bar of the patient having a large reference count can be readily identified. Since the display 7 displays comparison (for example, the certainty factor difference and the degree of the clinical change) between the analysis results based on the mathematical models before and after update, and the like for each of the patients to which the user such as a doctor often refers in the medical treatment process, the user can readily determine the validity of the mathematical models before and after update.

Figure 15:
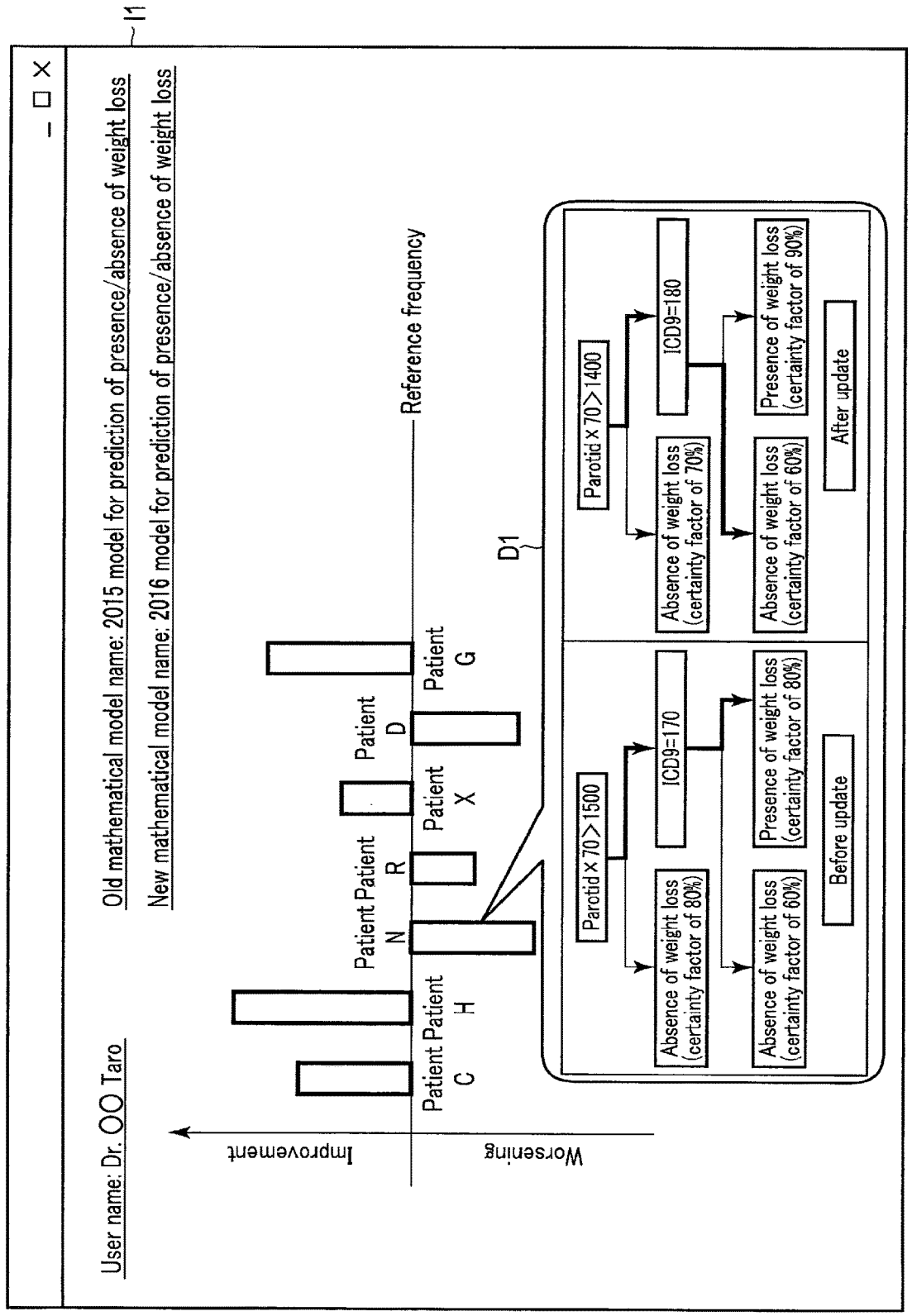
FIG. 15 is a view showing a verification screen on which detailed information of a patient N in FIG. 14 is superimposed.

The patient name or bar of each patient included in the verification screen I1 functions as a user interface, and is displayed to be selectable via the input interface 8. If the user designates a patient name or bar in the verification screen I1 via the input circuitry 8, the display 7 may display detailed information D1 of the patient corresponding to the designated patient name or bar, as shown in FIG. 15. FIG. 15 is a view showing the verification screen I1 on which detailed information D1 of a patient N is superimposed. As shown in FIG. 15, for example, a tree diagram of the mathematical model before update which shows a decision path and a tree diagram of the mathematical model after update which shows a decision path are displayed as the detailed information D1. Note that in FIG. 15, the decision paths are represented by thick arrows. As described above, when the display 7 displays, side by side, the tree diagrams of the mathematical models before and after update which show the decision paths, the user can more accurately determine the validity of the analysis results. The type of the detailed information D1 is not limited to the tree diagrams which show the decision paths. For example, tree diagrams which show no decision paths, the treatment result information of the patient, or the like may be displayed as detailed information.

Note that the display format of comparison of the analysis results is not limited to the graph format such as the verification screens shown in FIGS. 14 and 15, and may be a list format.

Figure 16:
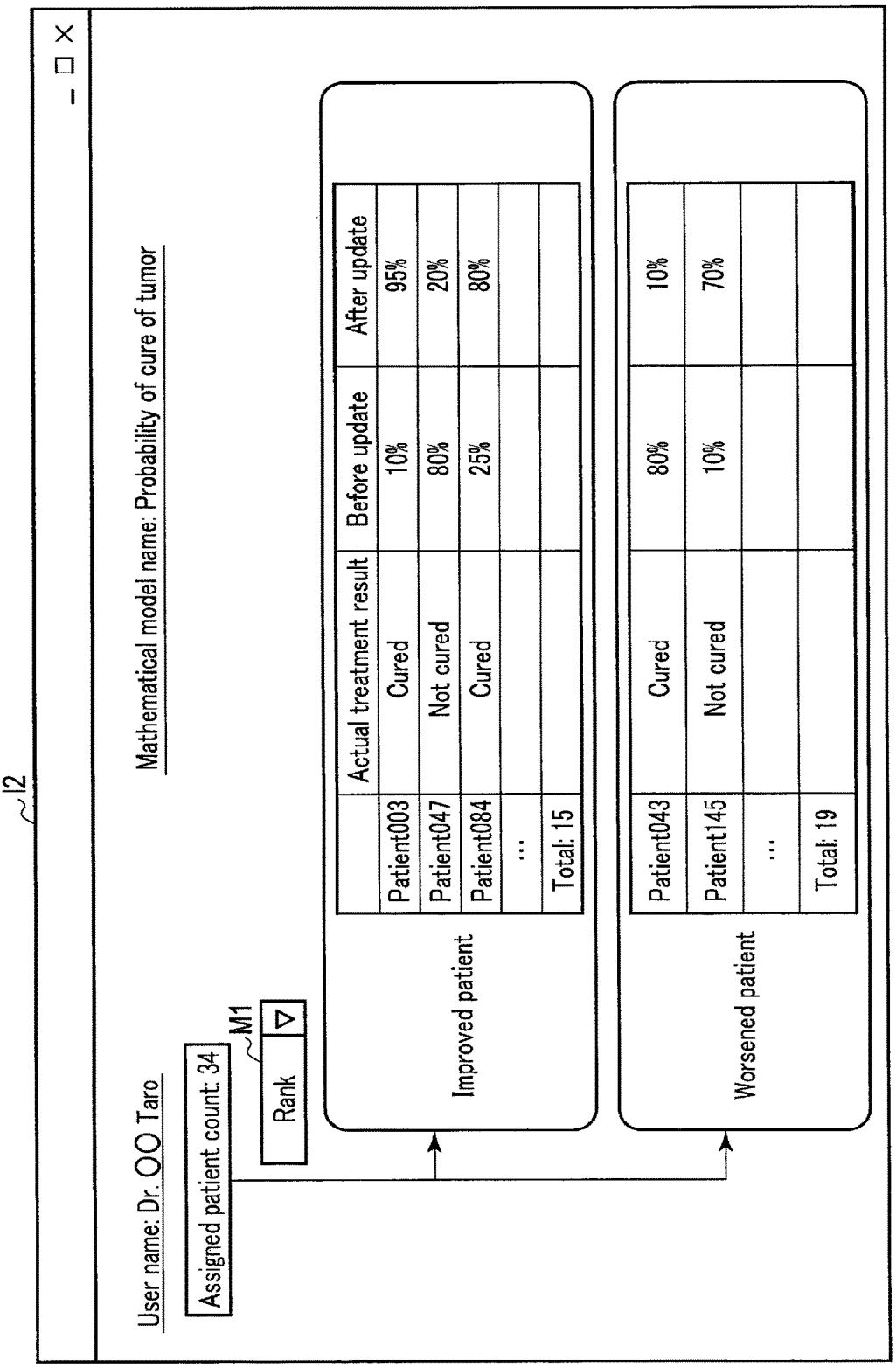
FIG. 16 is a view showing a verification screen in a list format generated in step S6 of FIG. 8.

FIG. 16 is a view showing a verification screen I2 in a list format. As shown in FIG. 16, the mathematical models before and after update are the mathematical models for the probability of cure of the tumor. The user of mathematical model verification processing is Dr. ○○ Taro. The comparison target patients are 34 patients assigned to Dr. ○○ Taro. As shown in FIG. 16, in the verification screen I2, a list of the actual treatment results, the probabilities of cure as the pre-update analysis results, and the probabilities of cure as the post-update analysis results of the respective patients is extracted for each of the degrees of the clinical changes (improvement and worsening). For each of "improvement" and "worsening", data are displayed from the top in descending order of the difference (certainty factor difference) between the probability of cure before update and that after update. That is, the data are displayed in descending order of the clinical change between the analysis results before and after update.

The display order of the patients is selectable from various viewpoints. For example, the verification screen I2 includes a pull-down menu M1 for selecting a viewpoint for the display order. The viewpoint for the display order is not limited to the descending (or ascending) order of the certainty factor difference, and may be the descending (or ascending) order of the analysis result value or the descending order of the reference count.

As described above, in the verification screen I2, comparison between the probability of cure based on the mathematical model before update and that based on the mathematical model after update is displayed for each patient to which the reference subject such as a clinician often refers in the medical treatment process. Therefore, even a person who is not well versed in statistics can determine whether the mathematical models before and after update are good or bad.

FIG. 17 is a view showing a verification screen I3 from another viewpoint. As shown in FIG. 17, the verification screen I3 shows statistics of the tendencies of the clinical changes between the pre-update analysis results and the post-update analysis results with respect to the comparison target patients. For example, the verification screen I3 shows, for each of the degrees of the clinical changes (improvement and worsening), the numbers of patients for respective ages for which the difference between the pre-update analysis result and the post-update analysis result is equal to or larger than 50%. The mathematical model is the probability of cure of the tumor. The display 7 displays a pull-down menu M2 capable of selecting a sort of the results from a viewpoint other than the age. The viewpoint other than the age may be the sex, the treatment apparatus, or any other viewpoint. The verification screen I3 displays patients limited to those each having a certainty factor difference of 50% or more but may display patients each having a difference equal to or larger or smaller than a numerical value other than 50%. The verification screen I3 displays, in a list format, the numbers of patients each having a certainty factor difference of 50% or more but may display them in a chart format such as a histogram or a distribution map.

The display 7 can display statistics of the tendencies of the clinical changes between the pre-update analysis results and the post-update analysis results with respect to the comparison target patients. Since the user often refers to the comparison target patients in daily medical treatment processes, he/she can understand the statistics well.

Mathematical model comparison executed by the processing circuitry 1 in accordance with the mathematical model comparison program has been described.

Note that various changes can be made for the processing procedure shown in FIG. 8. For example, the comparison target patient setting processing in step S4 may be provided before the analysis result. In this case, the analysis result calculation processing in step S2 and the accuracy index calculation processing in step S3 are performed only for the comparison target patients. Therefore, the analysis result calculation processing in step S2 and the accuracy index calculation processing in step S3 for a patient that is not involved in comparison between the analysis results can be omitted.

In step S1, mathematical models are constructed based on the basic model information and detailed model information stored in the mathematical model database 2. However, constructed mathematical models may be stored in the mathematical model database 2. In this case, in step S1, it is not necessary to perform mathematical model construction processing, and mathematical models before and after update are read out from the mathematical model database 2 based on the model ID or the like.

In this embodiment, the first and second mathematical models are compared. However, three or more mathematical models may be compared. For example, the processing circuitry 1 compares the mathematical model before update with mathematical model 1 after update, and further compares the mathematical model before update with mathematical model 2 after update by the same processing as that in the above embodiment. The processing circuitry 1 generates a verification screen simultaneously or parallelly showing the comparison result of the mathematical model before update and mathematical model 1 after update and the comparison result of the mathematical model before update and mathematical model 2 after update, and the display 7 displays the generated verification screen. This enables the user to readily verify/determine which of mathematical models 1 and 2 after update is better.

As described above, the radiotherapy planning apparatus 100 according to this embodiment includes the processing circuitry 1 and the display 7. The processing circuitry 1 calculates, by applying patient information to each of a plurality of analysis models relating to clinical practice, analysis results based on the analysis models. The processing circuitry 1 compares each of the analysis results with an actual clinical result relating to a comparison target patient, and generates evaluation information to evaluate a change between the analysis models. The display 7 displays the evaluation information.

In the first embodiment, the processing circuitry 1 applies the first and second mathematical models related to the treatment progress to each of pieces of patient information of a plurality of patients, thereby calculating the first analysis result based on the first mathematical model and the second analysis result based on the second mathematical model for each of the plurality of patients. The processing circuitry 1 sets comparison target patients from the plurality of patients. The processing circuitry 1 generates a verification screen showing, for each of the comparison target patients, the tendency of the clinical change between the first and second analysis results with reference to an actual treatment result. The display circuitry 7 displays the verification screen.

In accordance with the above arrangement, since the radiotherapy planning apparatus 100 according to this embodiment displays comparison between the analysis results based on the mathematical models before and after update for each of the comparison target patients, the user such as a doctor can readily and accurately determine the validity of the mathematical models before and after update without being well versed in statistics. As a result, it is possible to use mathematical models of high reliability, and thus the user can appropriately make a medical judgment for improving the QOL of each patient based on the analysis results of the mathematical models.

Therefore, it is possible to readily verify mathematical models related to clinical practice.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiotherapy planning apparatus comprising:
processing circuitry;
a storage device coupled to the processing circuitry; and
a display coupled to the processing circuitry, wherein:
the storage device is configured to store, for each of a plurality of patients, actual treatment information representing a treatment actually applied to the patient according to a radiotherapy plan and actual result information representing actual treatment progress of the patient associated with the treatment,
the processing circuitry is configured to:
acquire a plurality of analysis models for predicting treatment progress of a patent in a case where a radiotherapy plan is applied to the patient and outputting predicted result information representing the predicted treatment progress of the patient, each of the plurality of analysis models being formed using parameters relating to the radiotherapy plan;
for each of the plurality of analysis models, calculate the predicted result information of a target patient based on the analysis model by acquiring pieces of the actual treatment information of the target patient that correspond to the parameters used in the analysis model from the storage device and applying the analysis model to the acquired pieces of the actual treatment information of the target patient:
for each of the plurality of analysis models, acquire the actual result info(cation associated with the actual treatment information of the target patient from the storage device and calculate, based on the acquired actual result information and the predicted result information of the target patient, an accuracy index of the analysis model with respect to the target patient; and
for the target patient, generate evaluation information representing a change between the plurality of analysis models by comparing the accuracy indices of the plurality of analysis models with each other, and
the display is configured to display the evaluation information with respect to the target patient.

2. The radiotherapy planning apparatus of claim 1, wherein the processing circuitry is configured to set the target patient from the plurality of patients.

3. The radiotherapy planning apparatus of claim 2, wherein:
the storage device is configured to store reference tendency information representing a tendency of reference to medical information of the plurality of patients in a medical treatment process relating to the treatment for a user, and
the processing circuitry is further configured to set the target patient based on the reference tendency information.

4. The radiotherapy planning apparatus of claim 3, wherein the processing circuitry is configured to:
acquire a piece of the medical information which the user refers to and/or a medical treatment process which is performed at a time of reference, and
update the reference tendency information stored in the storage device based on the acquired piece of the medical information and/or the acquired medical treatment process.

5. The radiotherapy planning apparatus of claim 3, wherein:
the reference tendency information stored in the storage device includes, for at least one item of a sex of the patient, an age of the patient, a treatment portion of the patient, and a type of treatment apparatus used for the patient, a reference count for the medical information of each of the plurality of patients; and
the processing circuitry is configured to set, as the target patient, patients whose medical information has the reference count for a predetermined one of the at least one item, which is not smaller than a predetermined count.

6. The radiotherapy planning apparatus of claim 5, wherein the reference tendency information stored in the storage device includes the reference count for each department or each hospital.

7. The radiotherapy planning apparatus of claim 2, wherein the processing circuitry is configured to set, as the target patient, patients whose medical information is referred to during a latest predetermined period or patients whose medical infoimation is referred to during a specific past period.

8. The radiotherapy planning apparatus of claim 2, wherein:
the processing circuitry is configured to generate the evaluation information for each of a plurality of target patients;
the display is configured to display the evaluation information for each of the plurality of target patients in a chart: and
when the processing circuitry detects that a user designates one patient from the plurality of target patients shown in the chart, the processing circuitry causes the display to display detailed information of the designated patient.

9. The radiotherapy planning apparatus of claim 1, wherein:
each of the plurality of analysis models is configured to output the predicted result information representing a predicted result and a certainty factor that indicates a probability of the predicted result in a case where the radiotherapy plan is applied to a patient,
the processing circuitry is configured to:
for each of the plurality of analysis models, calculate the predicted result and the certainty factor for the predicted result information of the target patient based on the analysis model by applying the analysis model to the acquired pieces of the actual treatment information of the target patient; and
for the target patient, generate a degree of a clinical change and a certainty factor difference for the evaluation information based on the acquired actual result information, the predicted results, and the certainty factors obtained from the plurality of analysis models, and
the display is configured to display the degree of the clinical change and the certainty factor for the evaluation information with respect to the target patient.

10. The radiotherapy planning apparatus of claim 1, wherein:
the plurality of analysis models include a first analysis model and a second analysis model obtained by updating the first analysis model; and
the processing circuitry is configured to:
calculate first predicted result information by applying the first analysis model to the acquired pieces of the actual treatment information of the target patient that correspond to the parameters used in the first analysis model, and a second predicted result information by applying the second analysis model to the acquired pieces of the actual treatment information of the target patient that correspond to the parameters used in the second analysis model;

for the target patient, calculate a first accuracy index of the first analysis model based on the acquired actual result information and the first predicted result information and a second accuracy index of the second analysis model based on the acquired actual result information and the second predicted result information; and for the target patient, generate the evaluation information by comparing the first accuracy index of the first analysis model with the second accuracy index of the second analysis model.

11. The radiotherapy planning apparatus of claim 10, wherein the evaluation information indicates a degree of improvement or worsening of the second analysis model with reference to the first analysis model, or indicates whether the second analysis model is improved or worsened relative to the first analysis model.

12. The radiotherapy planning apparatus of claim 10, wherein the processing circuitry is configured to calculate a clinical change between the first analysis model and the second analysis model by comparing the first predicted result information and the second predicted result information with the acquired actual result information for the target patient.

13. The radiotherapy planning apparatus of claim 10, wherein the processing circuitry is configured to:

calculate a comparison index as the evaluation information that indicates the comparison between the first accuracy index and the second accuracy index; and generate a screen image to display the evaluation information on the display, the screen image schematically showing the comparison index for the comparison target patient.

14. The radiotherapy planning apparatus of claim 13, wherein the processing circuitry is configured to calculate, as the comparison index, a degree of a clinical change of the second predicted result information with respect to the first predicted result based on a difference between the first predicted result information and the second predicted result information with reference to the acquired actual result information.

15. The radiotherapy planning apparatus of claim 14, wherein the processing circuitry is configured to:

generate the evaluation information and calculate degrees of clinical changes between the first analysis model and the second analysis model for a plurality of target patients; and generate the screen image to be displayed on the display that shows differences between the first analysis model and the second analysis model for each of the plurality of target patients by visually discriminating the differences in accordance with the degrees of the clinical changes.

16. The radiotherapy planning apparatus of claim 14, wherein the processing circuitry is configured to:

generate the evaluation information and calculate degrees of clinical changes between the first analysis model and the second analysis model for a plurality of target patients; and generate the screen image that shows differences for each of the plurality of target patients in descending order of the degrees of the clinical changes between the first analysis model and the second analysis model.

17. The radiotherapy planning apparatus of claim 16, wherein the screen image includes the evaluation information of a limited patient, of the plurality of target patients, who has the degree of the clinical change greater than a threshold.

18. The radiotherapy planning apparatus of claim 1, wherein:

the processing circuitry is configured to generate a verification screen image showing a tendency of the change between the plurality of analysis models; and the display is configured to display the verification screen image.

19. A method of displaying, on a computer system, a result of comparison between a plurality of analysis models formed using parameters relating to a radiotherapy plan to predict treatment progress of a patent in a case where the radiotherapy plan is applied to a patient, the method comprising:

storing in a storage device, for each of a plurality of patients, actual treatment information representing a treatment actually applied to the patient according to the radiotherapy plan and actual result information representing actual treatment progress of the patient associated with the treatment;

acquiring the plurality of analysis models;

calculating predicted result information of a target patient based on each of the plurality of analysis models by acquiring pieces of the actual treatment information of the target patient that correspond to the parameters used in the analysis model from the storage device and applying the acquired pieces of the actual treatment information of the target patient to the analysis model;

for each of the plurality of analysis models, acquiring the actual result information associated with the actual treatment information of the target patient from the storage device and calculating, based on the acquired actual result information and the predicted result information of the target patient, an accuracy index of the analysis model with respect to the target patient;

for the target patient, generating evaluation information representing a change between the plurality of analysis models by comparing the accuracy indices of the plurality of analysis models with each other: and displaying the evaluation information with respect to the target patient.

20. The method of claim 19, wherein:

each of the plurality of analysis models is configured to output the predicted result information representing a predicted result and a certainty factor that indicates probability of the predicted result in a case where the radiotherapy plan is applied to a patient;

the calculating predicted result information of a target patient includes calculating, for each of the plurality of analysis models, the predicted result and the certainty factor for the predicted result information of the target patient based on the analysis model by applying the analysis model to the acquired pieces of the actual treatment information of the target patient;

the generating evaluation information includes generating, for the target patient, a degree of a clinical change and a certainty factor difference for the evaluation information based on the acquired actual result information, the predicted results, and the certainty factors obtained from the plurality of analysis models, and the displaying evaluation information includes displaying the degree of the clinical change and the certainty factor with respect to the target patient.

\* \* \* \* \*